United States Patent [19]

Antoinette et al.

[11] Patent Number: 5,281,322
[45] Date of Patent: Jan. 25, 1994

[54] ELECTROPHORESIS CASSETTE

[75] Inventors: Peter L. Antoinette, Littleton; John C. Caulmare, Acton, both of Mass.

[73] Assignee: Millipore Corporation, Bedford, Mass.

[21] Appl. No.: 108,860

[22] Filed: Aug. 18, 1993

[51] Int. Cl.⁵ .................. G01N 27/26; G01N 27/447
[52] U.S. Cl. .................. 204/299 R; 204/182.8; 204/180.1
[58] Field of Search .............. 204/299 R, 182.8, 180.1

[56] References Cited

U.S. PATENT DOCUMENTS

| 4,909,918 | 3/1990 | Bambeck et al. | 204/182.8 X |
| 5,164,065 | 11/1992 | Bettencourt et al. | 204/299 R |
| 5,232,573 | 8/1993 | Rosenveld | 204/180.1 X |

FOREIGN PATENT DOCUMENTS 1-69941  3/1989  Japan ........................ 204/299 R

*Primary Examiner*—John Niebling
*Assistant Examiner*—John S. Starsiak, Jr.
*Attorney, Agent, or Firm*—Andrew T. Karnakis; Paul J. Cook

[57] ABSTRACT

A cassette for conducting gel electrophoresis separation of samples is provided comprising two spaced apart flat plates wherein at least one flat plate has well spacers secured thereto.

A space between the plate is filled with an electrically conductive gel. The well spacers are electrically conductive.

8 Claims, 2 Drawing Sheets

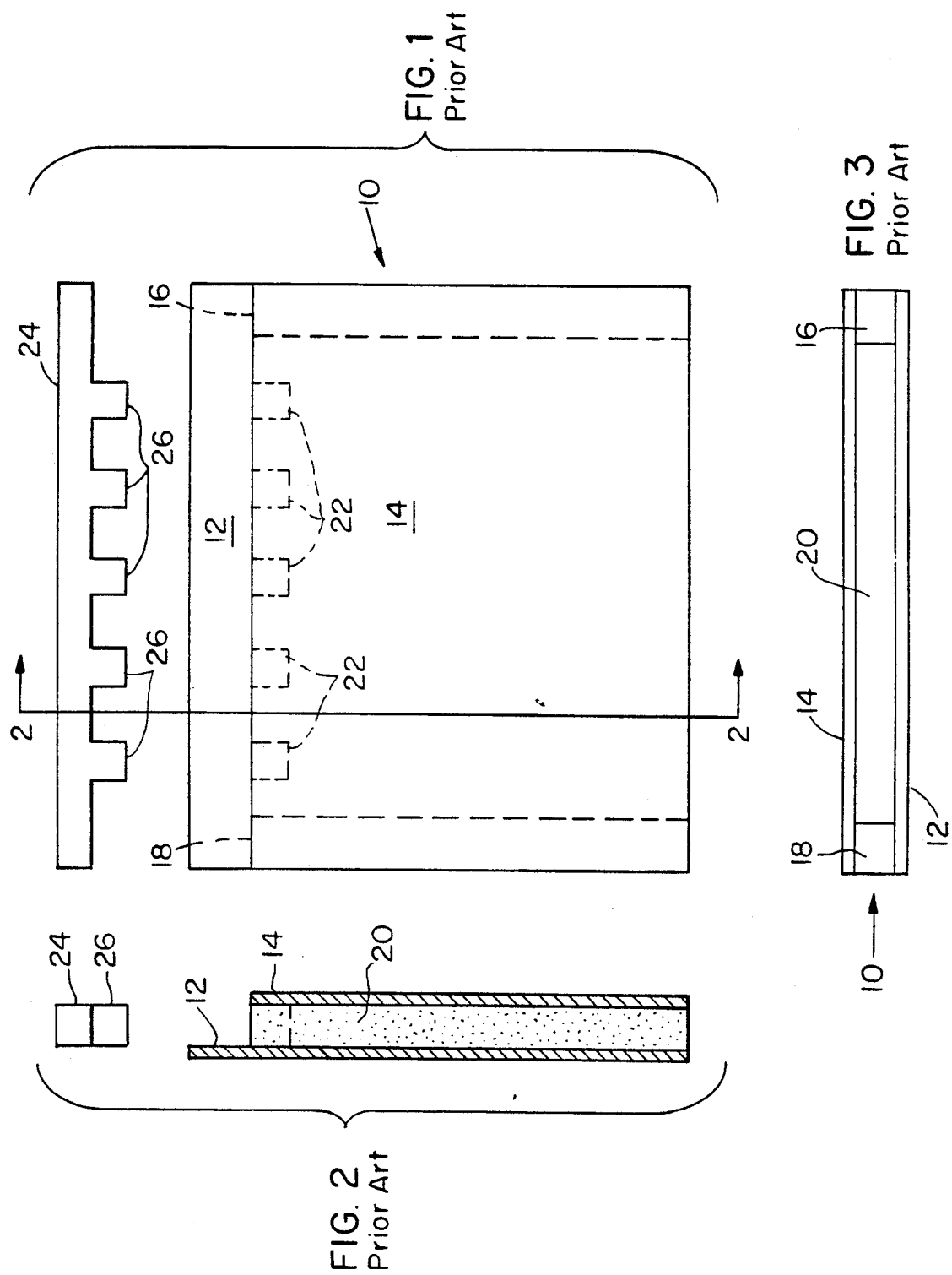

ELECTROPHORESIS CASSETTE

BACKGROUND OF THE INVENTION

This invention relates to an electrophoresis cassette useful for conducting gel electrophoresis separations.

Electrophoresis is the resolution of a complex mixture of macromolecules on the basis of charge and/or size under the influence of an electric field and is a primary tool in biochemistry, used to separate complex mixtures of molecules such as proteins or nucleic acids into their individual components. Electrophoretic analysis is based upon the fact that each molecule is characterized by a particular electrophoretic mobility under a given set of conditions. Macromolecules will migrate within a voltage gradient according to their net charge and will reach equilibrium at their isoelectric point at which their net mobility will be zero. For example, many proteins exhibit a net negative charge which is affected by the surrounding pH. When a mixture of proteins is placed in a support medium, such as a buffered gel, which is subjected to a voltage gradient, each component is caused to migrate through the support medium at its characteristic rate for that set of conditions. Electrophoretic mobility is a function of other factors which are controlled by experimental conditions.

It is common practice to conduct electrophoresis in a buffered gel positioned between two flat plates, usually transparent glass or plastic and separators between the plates which provide essential support for the gel. In order to provide accurate sample resolution, it is necessary that the gel composition be uniform and that the gel thickness be uniform. These conditions are necessary in order to avoid factors which affect molecular electrophoretic mobility other than the characteristics of the molecules being separated. In use, the cassette is positioned between two buffer solutions after the sample or samples have been placed on one gel surface. A voltage is applied between the buffers which causes the samples to migrate within the gel. Upon completion of sample preparation, the gel is separated from the plates for analysis.

Presently, a cassette is produced wherein a void volume is formed between two plates separated by two separators. A suitable separation gel medium such as agarose or a polyacrylamide is poured, in liquid form, into the void volume and allowed to polymerize therein. During formation of the gel, the two plates are compressed to the separators to prevent leakage of the gel material from the void volume and to assure a uniform distance between the plates, which, in turn, assures a uniform gel thickness.

In order to form sample wells at a top end of the cassette, a removable piece having fingers having the desired shape of the wells is positioned at the top end so that the fingers extend into the separation medium while it is polymerizing. After the gel is formed, the fingers are removed from the gel to leave wells wherein samples can be positioned. The use of this removable piece is undesirable since an additional apparatus is required and its use requires an additional manipulative step which must be conducted with care in order to avoid ripping the gel.

Accordingly, it would be desirable to provide a means for forming wells in the gel portion of a cassette which eliminates the need for a piece which must be removed subsequent to gel formation. In addition, it would be desirable to provide such a means which provides a uniform electrical resistance or field so that separation of samples can be maintained during gel electrophoresis.

SUMMARY OF THE INVENTION

The present invention provides a gel electrophoresis cassette comprising two plates, two separators positioned between the plates and an electrically conductive gel positioned between the plates and separated. A plate is provided with electrically conductive structures which extend from an inner surface of the plate to contact a second plate. The electrically conductive structures are spaced apart from each other a distance to define a well into which a sample. The structure can be rendered electrically conductive by forming them from an electrically conductive material by providing a pathway through the structure into which an electrically conductive material can be positioned in contact with the gel. The electrically conductive material can be the same composition as the gel.

BRIEF DESCRIPTION OF THE DRAWINGS

FIG. 1 is a plan view of a prior art cassette with a mold used to form wells in a gel.

FIG. 2 is a cross-sectional view of the prior art cassette of FIG. 1 taken along line 202.

FIG. 3 is a bottom view of the prior art cassette of FIG. 1.

DESCRIPTION OF SPECIFIC EMBODIMENTS

Figures 4, 5:
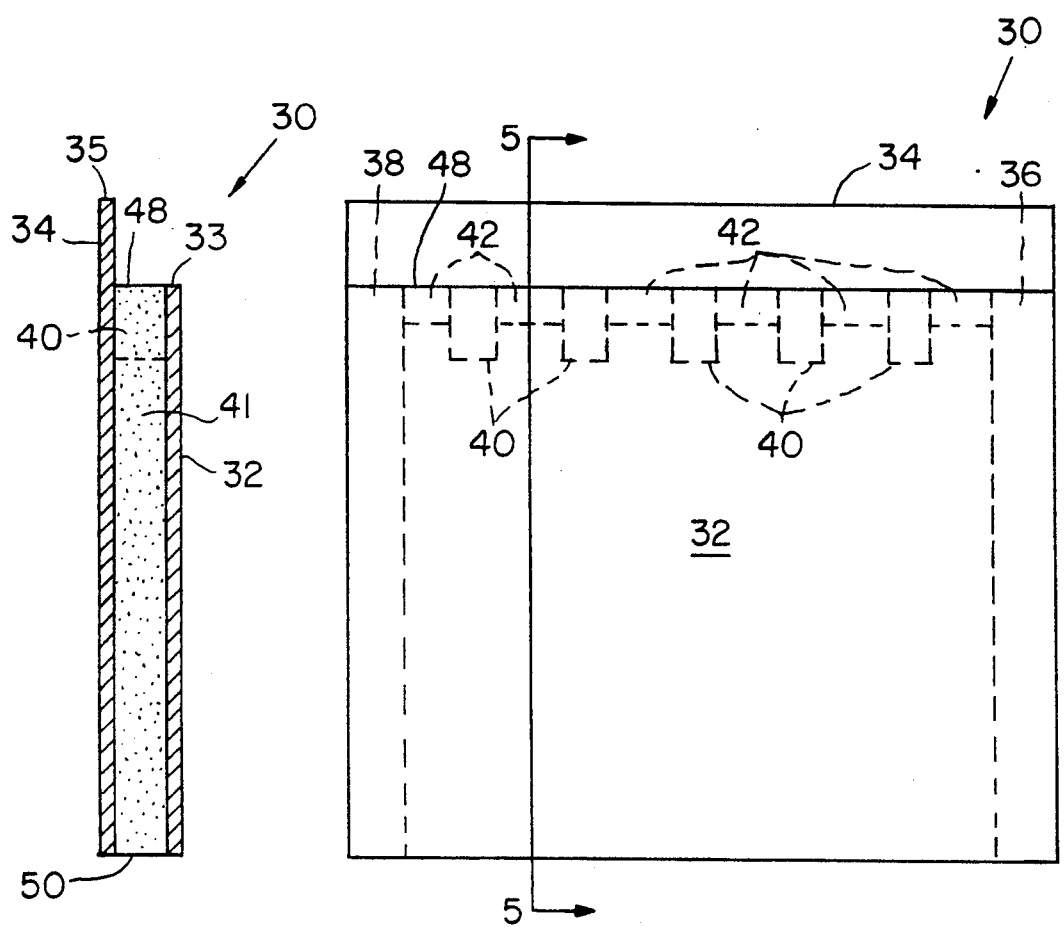
FIG. 4 is a plan view of the cassette of this invention.
FIG. 5 is a cross-sectional view of the cassette of FIG. 4 taken along line 5—5.

Referring to FIGS. 1-3, the gel electrophoresis cassette of the prior art 10 is shown. The cassette is formed from two flat plates 12 and 14, two spacers 16 and 18 and a gel layer 20 positioned between plates 12 and 14 and spacers 16 and 18. The wells 22 are formed by placing mold piece 24 having fingers 26 between plates 12 and 14. The gel precursor composition is provided between plates 12 and 14 while the bottom surfaces of the plates 12 and 14 and spacers 16 and 18 are sealed until the gel forms. Subsequent to gel formation, the mold piece 24 is carefully removed from the gel 20 to effect formation of wells 22. When the mold piece 24 is not carefully removed, tears will view in gel 20 so that the wells 22 will be irregularly formed thereby rendering the gel cassette 10 useless for its intended purpose. Irregular shaped wells 22 will increase the possibility of sample components from adjacent wells 22 of merging as the samples proceed through the gel 20.

Figure 6:
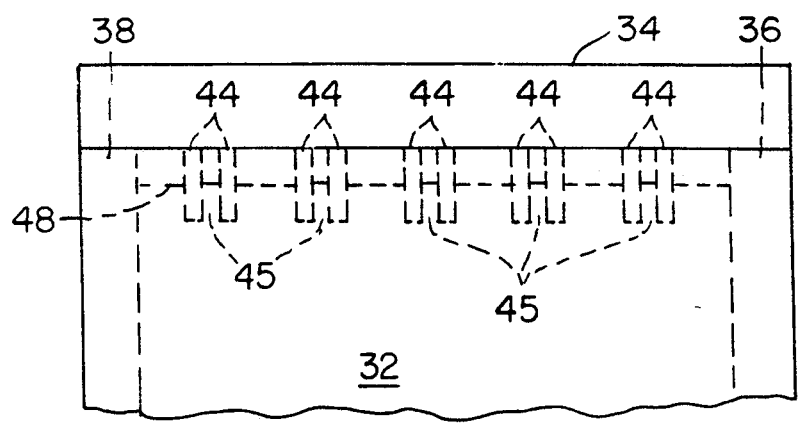
FIG. 6 is a partial plan view of an alternative cassette of this invention.

Referring to FIGS. 4-6, the gel cassette 30 of this invention is formed from two plates 32 and 34, spacers 36 and 38 and gel 41. The plate 32 has a top surface 33 and plate 34 has a top surface 35. The plates 32 and 34 can have the same length or can have different lengths as shown in FIGS. 4-6. Either the plate 32 or the plate 34 or both plates 32 and 34 have well spacers 40 integrally formed therewith in order to define wells 42 which are also defined by the plates 32 and 34. The well spacers can be solid as shown in FIG. 4 and formed of an electrically conductive material which is formed integrally with either or both plates 32 and 34 either by being molded therewith or adhered thereto. Alternatively, the well spacers 44 can bee formed of an electrically nonconductive material such as the same material used to form the plate 32 or 34 and which have spaced apart segments with a channel 45. In this embodiment, electrical conductivity for the well spacers 44 is effected by filling the spacers 45 with the electrically conductive gel 41. The spacer 45 has a width to permit inclusion of a sufficient amount of electrically conductive gel as to render the well spacer 44 sufficiently electrically conductive as to prevent admixture of samples from adjacent wells during the electrophoresis process.

Electrophoresis is conducted by applying an electrical voltage between the top surface 48 of the gel and the bottom surface 50 of the el in order to promote migration of sample components into the el thereby to stratify the sample components within the gel. The gel can be formed of any conventional electrically conductive gel composition such as a buffered polyacrylamide gel. After electrophoresis is completed, the plates 32 and 34 are separated from each other and the gel 50 containing separated samples is processed further by means conventional in the art.

We claim:

1. A cassette for conducting electrophoresis which comprises:

a first flat plate, having a first top surface and a first bottom surface, a second flat plate having a second top surface and a second bottom surface, first and second spacers positioned between said first plate and said second plate to define a space between said first plate and said second plate, and third spacers adapted to be electrically conductive positioned between said plates adjacent at least one of said first top surface or said second top surface and secured to at least one of said first plate or said second plate, said electrically conductive spacers being spaced apart from each other.

2. The cassette of claim 1 wherein said space is filled with an electrophoresis gel.

3. The cassette of claim 1 wherein said third spacers are formed from an electrically conductive composition.

4. The cassette of claim 2 wherein said third spacers are formed from an electrically conductive composition.

5. The cassette of claim 1 wherein said third spacers are formed from spaced-apart spacer segments having a second space therebetween, said third spacer being rendered electrically conductive by filling said second space with an electrically conductive composition.

6. The cassette of claim 2 wherein said third spacers are formed from spaced-apart spacer segments having a second space therebetween, said third spacer being rendered electrically conductive by filling said second space with an electrically conductive composition.

7. The cassette of claim 5 wherein said electrically conductive composition is an electrically conductive gel.

8. The cassette of claim 6 wherein said electrically conductive composition is an electrically conductive gel.

* * * * *